United States Patent
Almosa

(10) Patent No.: US 9,563,232 B2
(45) Date of Patent: Feb. 7, 2017

(54) WRIST-MOUNTED DEVICE TO ASSIST PILGRIMS

(71) Applicant: UMM AL-QURA UNIVERSITY, Makkah (SA)

(72) Inventor: Wedyan Hassan Essa Almosa, Makkah (SA)

(73) Assignee: UMM AL-QURA UNIVERSITY, Makkah (SA)

( * ) Notice: Subject to any disclaimer, the term of this patent is extended or adjusted under 35 U.S.C. 154(b) by 316 days.

(21) Appl. No.: 14/309,816

(22) Filed: Jun. 19, 2014

(65) Prior Publication Data

US 2015/0370285 A1 Dec. 24, 2015

(51) Int. Cl.

| | |
|---|---|
| *G09B 19/00* | (2006.01) |
| *A61B 5/11* | (2006.01) |
| *G06F 1/16* | (2006.01) |
| *G01J 3/02* | (2006.01) |
| *A47G 33/00* | (2006.01) |
| *G09B 5/06* | (2006.01) |
| *G04G 21/02* | (2010.01) |
| *G04G 11/00* | (2006.01) |
| *G04G 13/02* | (2006.01) |
| *G04G 21/04* | (2013.01) |

(Continued)

(52) U.S. Cl.
CPC ............. *G06F 1/163* (2013.01); *A47G 33/008* (2013.01); *A61B 5/0022* (2013.01); *G01J 3/0275* (2013.01); *G04G 11/00* (2013.01); *G04G 13/02* (2013.01); *G04G 21/025* (2013.01); *G04G 21/04* (2013.01); *G06F 1/1637* (2013.01); *G09B 5/06* (2013.01); *G09B 19/00* (2013.01); *A61B 5/02438* (2013.01); *A61B 5/1112* (2013.01); *A61B 5/681* (2013.01); *A61B 5/746* (2013.01); *A61B 2503/12* (2013.01)

(58) Field of Classification Search
CPC . A61B 5/0022; A61B 5/02438; A61B 5/1112; A61B 5/681; A61B 5/746; A47G 33/008; G01J 3/0275; G09B 5/06; G09B 19/00
USPC ........................................................ 434/245
See application file for complete search history.

(56) References Cited

U.S. PATENT DOCUMENTS

| | | | | |
|---|---|---|---|---|
| 6,100,806 A | * | 8/2000 | Gaukel | ............... B60R 25/1004 340/10.41 |
| 8,519,845 B2 | | 8/2013 | Mohandes | |

(Continued)

FOREIGN PATENT DOCUMENTS

| | | |
|---|---|---|
| CH | 683483G A3 | 3/1994 |
| WO | WO 2013/054161 A1 | 4/2013 |

OTHER PUBLICATIONS

Hamhoum, F. f., & Kray, C. c. (2012). Supporting pilgrims in navigating densely crowded religious sites. Personal & Ubiquitous Computing, 16(8), 1013-1023.*

*Primary Examiner* — Nikolai A Gishnock
(74) *Attorney, Agent, or Firm* — Richard C. Litman

(57) ABSTRACT

The wrist-mounted device to assist pilgrims is an electronic device worn on the wrist that provides functions to assist a pilgrim, particularly a pilgrim on a pilgrimage to a holy site. The device includes a heart rate monitor that alerts the user when his or her heart rate is too high, a GPS unit showing the location of holy sites of interest, a monitor for keeping a count of the number of perambulations around a holy site, e.g., when performing a Tawaf, an audio playback device that will play back a prayer or scripture, such as the Dua'a, and an annunciator for announcing prayer times.

7 Claims, 6 Drawing Sheets

(51) Int. Cl.
  *A61B 5/024* (2006.01)
  *A61B 5/00* (2006.01)

(56) References Cited

U.S. PATENT DOCUMENTS

| | | | |
|---|---|---|---|
| 9,282,843 B1* | 3/2016 | Al-Anzi | A47G 33/02 |
| 9,286,511 B2* | 3/2016 | Chung | G06K 9/00362 |
| 9,342,965 B2* | 5/2016 | Elgebaly | G06Q 10/06 |
| 2004/0013043 A1 | 1/2004 | Haq | |
| 2005/0285747 A1* | 12/2005 | Kozlay | G08B 21/22 340/573.4 |
| 2006/0253010 A1 | 11/2006 | Brady et al. | |
| 2007/0067054 A1* | 3/2007 | Danish | A47G 33/008 700/94 |
| 2007/0293374 A1 | 12/2007 | Chan | |
| 2011/0014929 A1* | 1/2011 | Moshfeghi | H04W 4/02 455/456.3 |
| 2012/0101883 A1* | 4/2012 | Akhter | G06Q 30/0215 705/14.17 |
| 2012/0154146 A1* | 6/2012 | Mohandes | G08B 21/0275 340/539.13 |
| 2013/0053056 A1* | 2/2013 | Aggarwal | G01S 5/0263 455/456.1 |
| 2013/0316723 A1* | 11/2013 | Alwakeel | H04W 4/02 455/456.1 |
| 2015/0269134 A1* | 9/2015 | Cochran | G06F 17/30038 715/233 |
| 2015/0370285 A1* | 12/2015 | Almosa | G04G 21/025 434/245 |
| 2016/0242680 A1* | 8/2016 | Arif | A61B 5/1112 |

* cited by examiner

WRIST-MOUNTED DEVICE TO ASSIST PILGRIMS

BACKGROUND OF THE INVENTION

1. Field of the Invention

The present invention relates to a medical and tracking device, and particularly to a wrist-mounted device to assist pilgrims, especially pilgrims who come to Mecca (Makkah) to make the Hajj and Umrah pilgrimages.

2. Description of the Related Art

The most important concern for an Islamic individual in the performance of religious rituals, such as Hajj and Umrah during Ramadan and Hajj holy days, is to adhere to the rituals as prescribed in the individual's religious community. Some rituals require the individual or pilgrim to circle a holy site (e.g., the Kaaba or Ka'aba, the most sacred site in Islam, the circling being part of a ritual known as the Tawaf) a certain number of times and also chant or listen to a prayer devoted to their religious rites. The Hajj is usually performed in the twelfth month of the Islamic calendar, and should be performed at least once during an Islamic person's lifetime. The Umrah may be performed at any time of the year, but is often performed during the last ten days of Ramadan. The injunction for compliance with the requirements of the rituals is the same, whether the individual is young or elderly.

Thus, Mecca is often crowded with pilgrims who have come to perform the rites of their religion during the holy days of the Hajj and Ramadan. The congested conditions, together with the hot climate and the physical exertion of the rites, raises concerns about the health of the visitors, particularly the elderly, as well as directing the pilgrims to the sites where the rites are to be performed, and other matters relating to ensuring that the rites have been observed.

Thus, a wrist-mounted device to assist pilgrims solving the aforementioned problems is desired.

SUMMARY OF THE INVENTION

The wrist-mounted device to assist pilgrims includes an apparatus and also includes a method for operating the device to assist in performing religious rituals. The device is designed to have many useful functions and provide useful information, for example, measuring heart pulse rates, detecting a light source, counting the number of complete rotations, providing alerts, providing an audio outlet, storing personal information about the individual and providing directional information to specific locations using a GPS navigational system.

Processors, GPS chips, and sensors are placed in the casing and along the wrist-mounted device's strap of the wrist-mounted device to assist in performing religious rituals. The processor and sensors are capable of detecting and monitoring an individual's health vitals, such as heart rate, and alert the individual if the health vitals are outside of a defined parameter. The detection of heart rate allows an individual, such as an elderly person, to monitor their heart rate and temporarily halt his or her rotation or ambulation around the holy site until their heart rate is back within a pre-defined normal range. The processor, GPS chip and sensors are also capable of detecting the initial or start point in a holy site to indicate to the individual or pilgrim where to start performance of religious rituals.

The wrist-mounted device also allows the individual to listen to an audio transmission incorporating religious chants, such as a collection of prayers. This allows the individual to continue prayers for supplication during the performance of the ritual and obviates the need to read prayers of supplication from books while performing religious rituals, such as completing a number of rotations around the religious site.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Referring to FIGS. 1A to 5 of the drawings, the wrist-mounted device 100 to assist pilgrims takes the form of a wristwatch having a case 101 and attachment means, such as watch straps 114, for attaching the case around a wrist of a pilgrim. Generally stated, the attachment means is adapted to extend around part of the individual's arm or wrist. In an alternative embodiment, the attachment means can be adapted to loop around the individual's neck or waist, or for attachment to an article of clothing.

The wrist-mounted device 100 may include an LCD display 110 for displaying data, such as heart rate, personal information, audio data, or GPS location. The wrist-mounted device 100 also has a number of push buttons for operation of the device and data input of personal information, such as the pilgrim's age, height, weight, physical condition, address, health issues, and other health or private information.

Figure 1A:
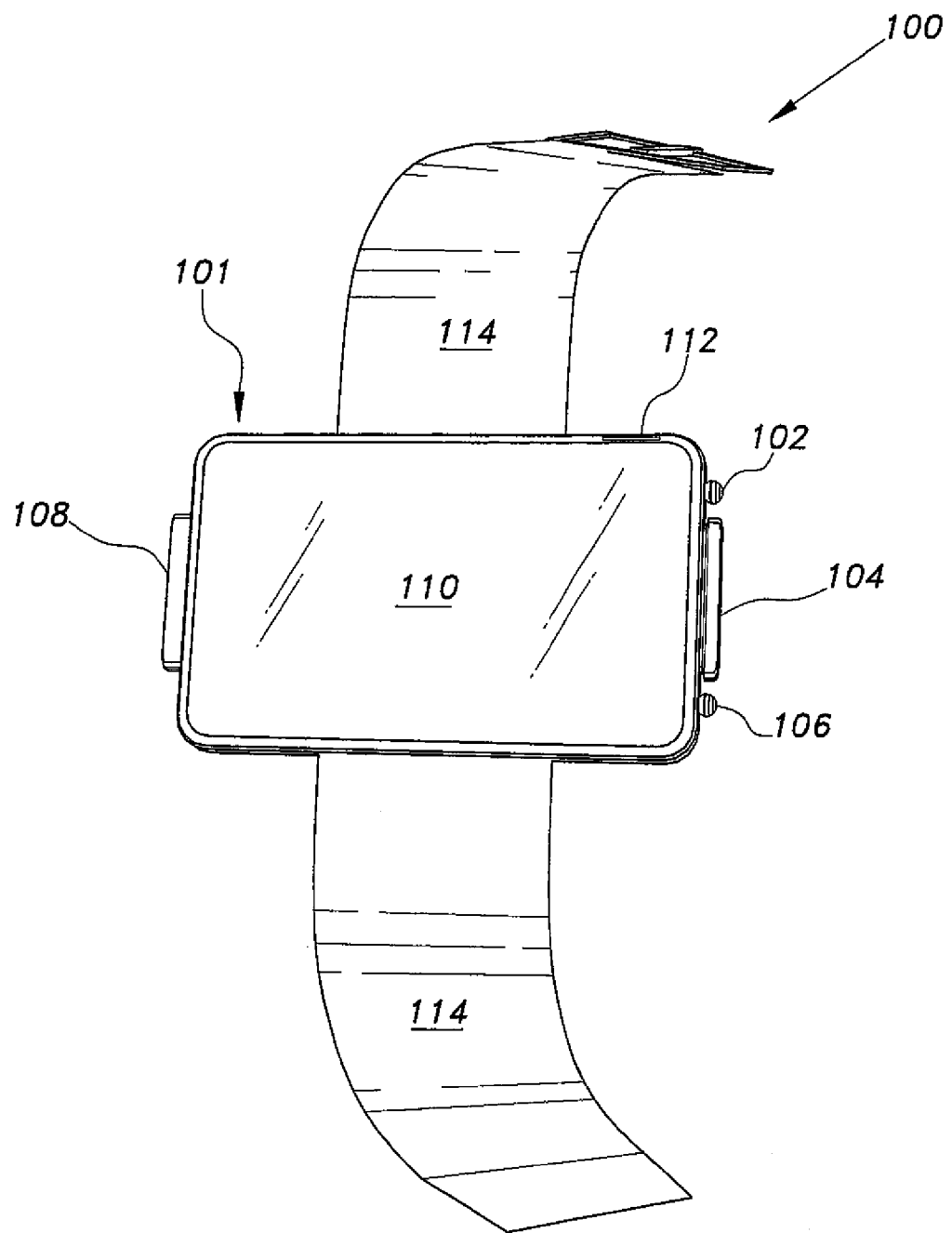
FIG. 1A is a perspective view of a wrist-mounted device according to the present invention.

Referring to FIG. 1A, the wrist-mounted device 100 may have a case 101, an LCD activation button 102, a rotation count button 104, a location button 106, an audio control button 108, an LCD display 110, a sensor 112, and watch straps 114. The case 101 is preferably made of plastic, but is not limited in this regard, and any suitable material known in the art can be substituted. The watch straps 114 can be made of any suitable material, such as cloth, fabric, plastic, or a combination thereof, and is not limited in this regard. The fastening of the watch straps can be accomplished by various fastening means, such as a clasp, a zipper, or a button, and is not limited in this regard. The LCD display 110 can be any type of electronic visual or digital display adapted for use with an electronic processor. The wrist-mounted device 100 operates under the control of the processor housed in the case 101, which is programmed to perform various functions in different operating modes. For example, the processor provides the ability to monitor heart rate, play audio and display information onto the LCD display 110. Furthermore, personal information can be inputted into the processor by an individual by means of a capacitance touch screen or multi-touch interface, as known in the art, and can incorporate the use of a digital or virtual keyboard.

Figure 1B:
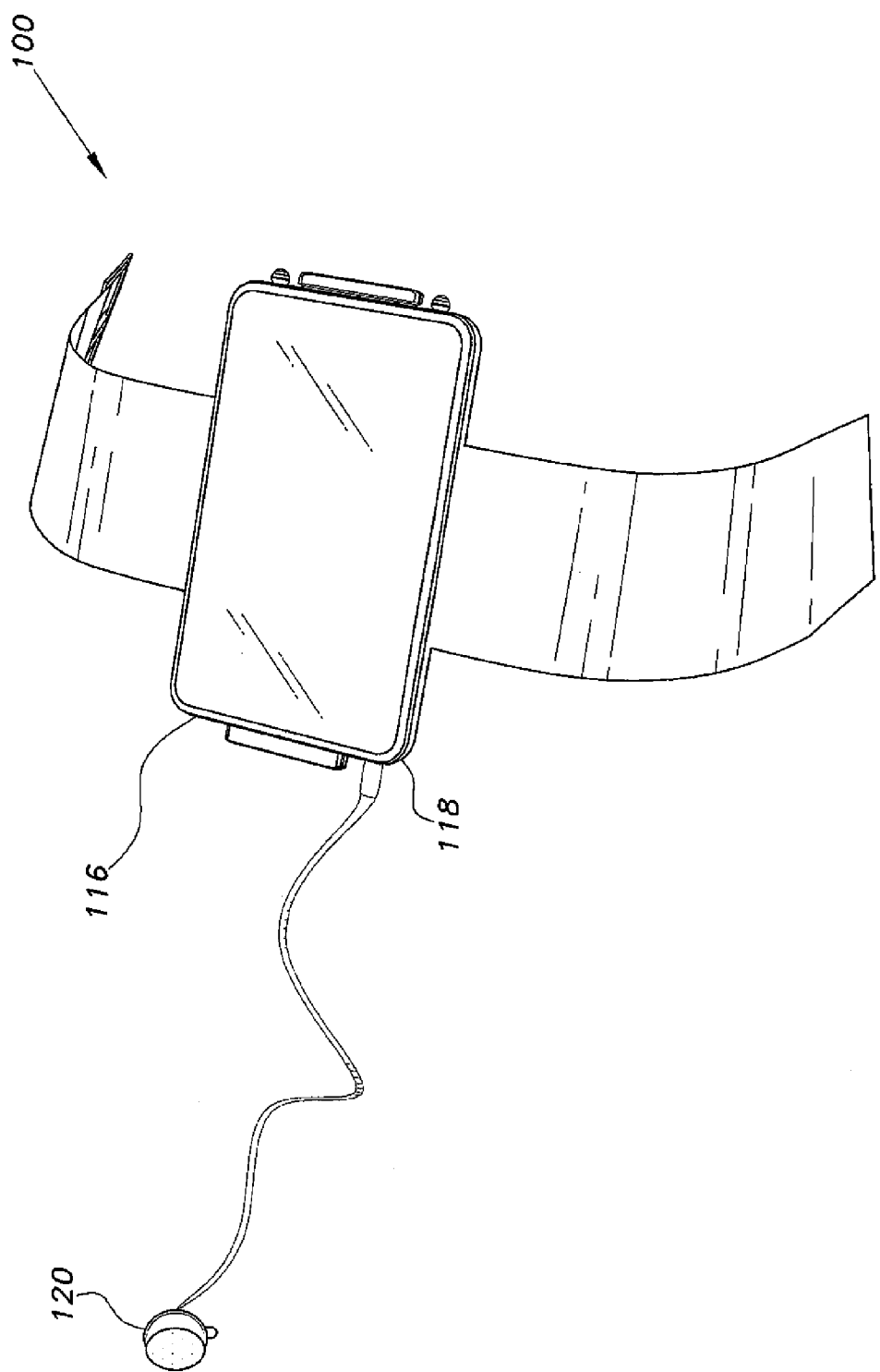
FIG. 1B is another perspective view of the wrist-mounted device of FIG. 1A.

As shown in FIG. 1B, the device 100 may have a charging port 116, an audio outlet 118, and ear buds 120. The audio outlet 118 can be for any type of connector, such as an audio jack, phone jack, phone plug, headphone jack plug, microphone jack, tiny telephone connector, or bantam plug. The audio outlet 118 is adapted for use with the standard 3.5 mm connector plug, but can be adapted for use with various sizes of connector plugs or earphones, such as those using a 2.5 mm plug, a 6.35 mm plug, or a 310 connector plug.

Figure 2:
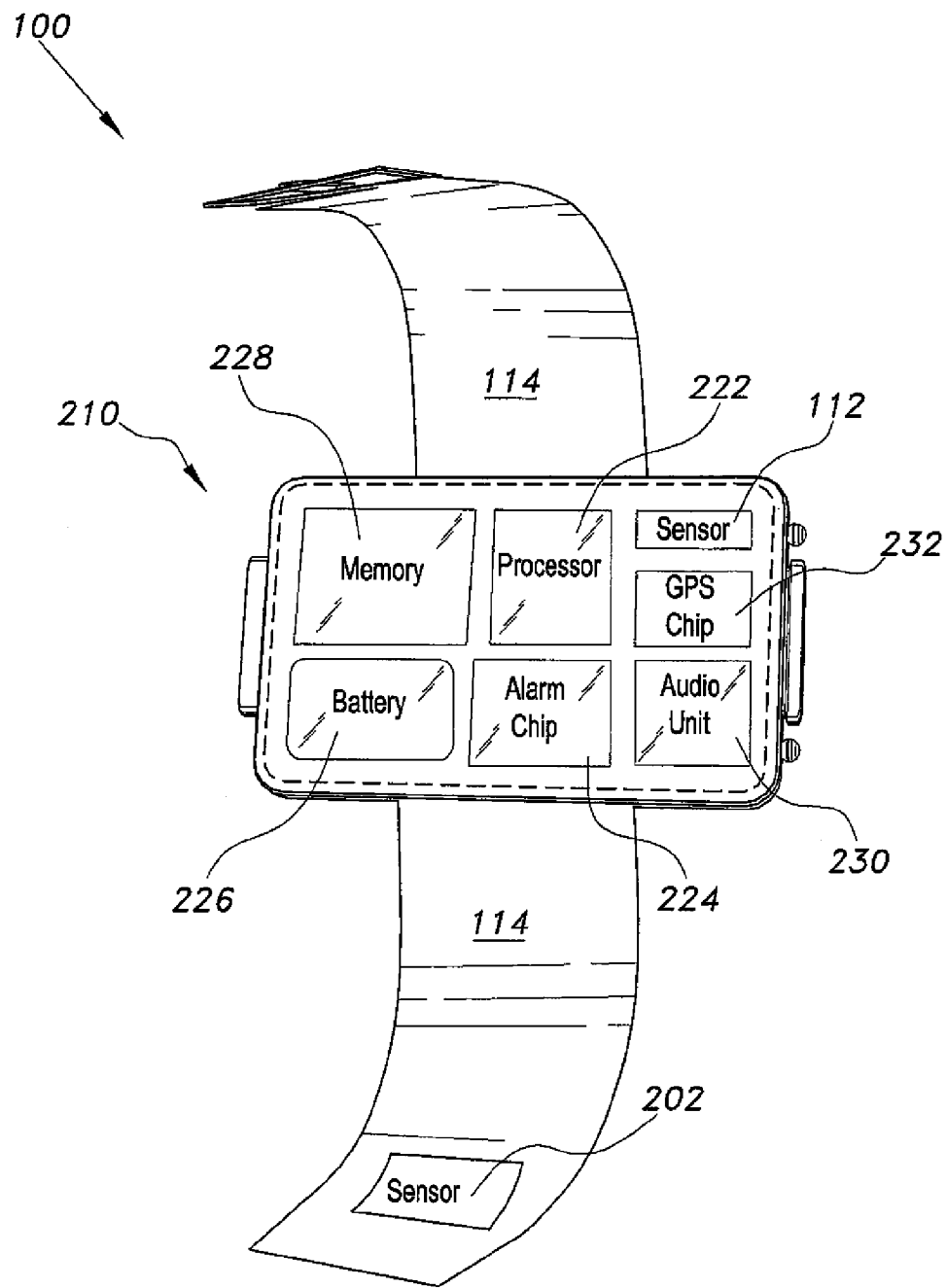
FIG. 2 is perspective view the wrist-mounted device of FIG. 1A with the back of the case removed to show the electronic circuits.

As shown in FIG. 2, inside the case 101, there is a generalized system and control unit 210 that includes a processor 222, the sensor 112, an alarm chip 224, a battery 226, a memory 228, an audio unit 230, and a GPS chip 232. The processor 222 may be a microprocessor, microcontroller, digital signal processor, application specific integrated circuit (ASIC), or any other integrated circuit configured to carry out the functions described herein. The individual's personal information, such as the individual's age, weight, height, etc. can be inputted through the LCD display 110, such as through a virtual digital keyboard displayed on the capacitance touchscreen. The personal information or data can be transmitted from or received by an interface, such as the LCD display 110, including received GPS data and personal information, for example. Such information or data can be organized and stored in the memory 228 and transmitted to or from the memory 228, such as a computer readable memory, which can be any suitable type of non-transitory computer readable and programmable memory, to the processor 222. The battery 226 may be a disposable dry cell battery, or may be a rechargeable battery that can be coupled to a charging device or connected or coupled to a standard outlet for electrical power, for example.

Examples of computer readable media as can be used or included in the memory 228 can include a non-transitory computer readable storage memory, a magnetic recording apparatus, an optical disk, a magneto-optical disk, and/or a semiconductor memory (for example, RAM, ROM, etc.). Examples of magnetic recording apparatus that may be used in addition to memory 228, or in place of the memory 228, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

The entering of personal information or GPS data can also be transferred or obtained by USB connection or any suitable form that allows data transfer. The information and operations that are transmitted throughout the various embodiments of a wrist-mounted device 100 to assist in performing religious rituals or methods for operating the wrist-mounted device 100 can be in the form of electronic data, wireless signals, or a variation thereof. The information, such as GPS data, and operations that are transmitted throughout the various embodiments can be sent wirelessly, optically, or by any of various types or arrangements of hard-wire connections, or combinations thereof.

The GPS (Global Positioning System) chip is a device that uses a satellite-based navigation system based on signals and coordinates that are tracked by various satellites, such as those orbiting the earth. The audio unit 230 can include a speaker or an audio outlet 118 for use with earphones.

The processor can also send a signal to the alarm chip and the audio unit to provide at least one type of sensory feedback to the individual, such as an audio alert or sound from the audio output unit 218, or a picture or written message from the LCD display 110, such as if the individual's heart rate is outside of a predefined parameter. The predefined parameter can be preprogrammed into the memory or entered into the memory by the individual through the LCD display.

Also illustrated in FIG. 2 is a sensor 202, which is housed in the attachment means, such as the wrist straps 114. The sensor 202 can be attached to an individual to detect and obtain an individual's heart rate by detecting the individual's heart rate pulse. Although FIG. 2 illustrates two sensors, it is not limited in this regard, and additional sensors can be added.

Figure 3:
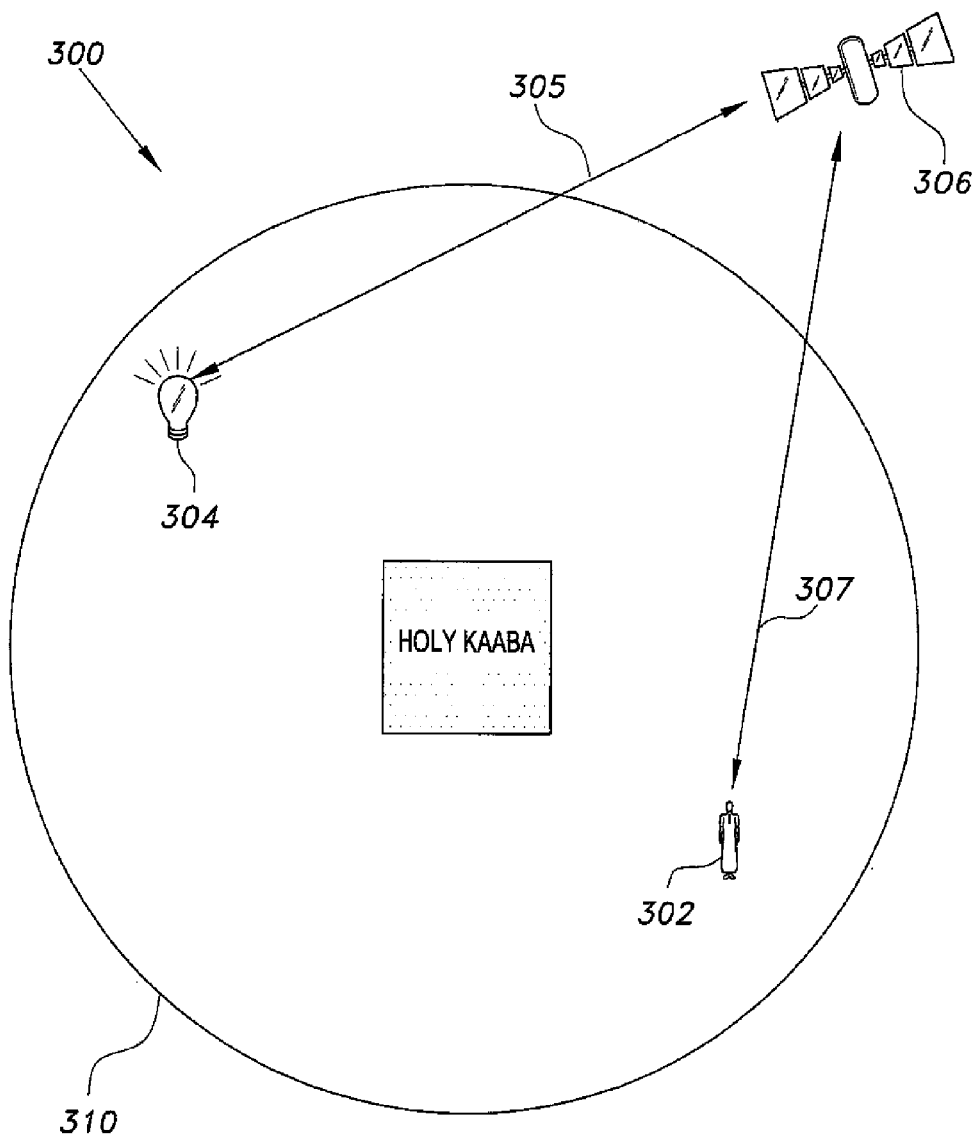
FIG. 3 is a diagram illustrating use of the wrist-mounted device of FIG. 1A to comply with some requirements of religious ritual.

FIG. 3 schematically shows an exemplary depiction of an individual 302 walking around a cuboid building at the center of a mosque 310. In this example, the cuboid building is titled "Holy Kaaba" and is used to exemplify the religious site for worshippers of the Islamic religion. In the Islamic religion, religious followers are expected to travel to the most sacred mosque, Al-Masjid al-Haram, in Mecca, Saudi Arabia at least once in the follower's lifetime and follow the Islamic rituals of pilgrimage. For example, during the Hajj and Umrah holy days, Islamic followers are expected to circumambulate the Kaaba seven times, in a counterclockwise direction.

FIG. 3 schematically shows the individual 302, a light source 304, and a satellite 306. The light source 304 indicates one location that is traditionally designated a start point for the followers of Islam to start their circumambulation around the Kaaba in a counterclockwise fashion. The light source indicating the traditional start point around the Kaaba is usually shown as a green light in the Islamic religion, but is not limited in this regard.

The individual 302 wearing the wrist-mounted device 100 can receive and send coordinates 307 to and from the satellite 306 via the wrist-mounted device. The satellite can receive the coordinates 305 of the traditional start point for rotations around the Kaaba, which is usually indicated by a green light, such as the light source 304 in FIG. 3. This green light is also an indicator for the individual that he or she has completed a full rotation around the holy site, such as Kaaba. The processor 222 in the wrist-mounted device 100 can register each time the GPS chip 232 is in a close location to the light source 304 as detected by the sensor 112 in order to count the number of complete rotations the individual has done. The sensor 112 can detect the color of the light source, such as a green light, for determining the number of complete rotations. Each time the sensor detects the light source 304, data signals are sent to the processor 222 to track the number of complete rotations.

Figure 4:
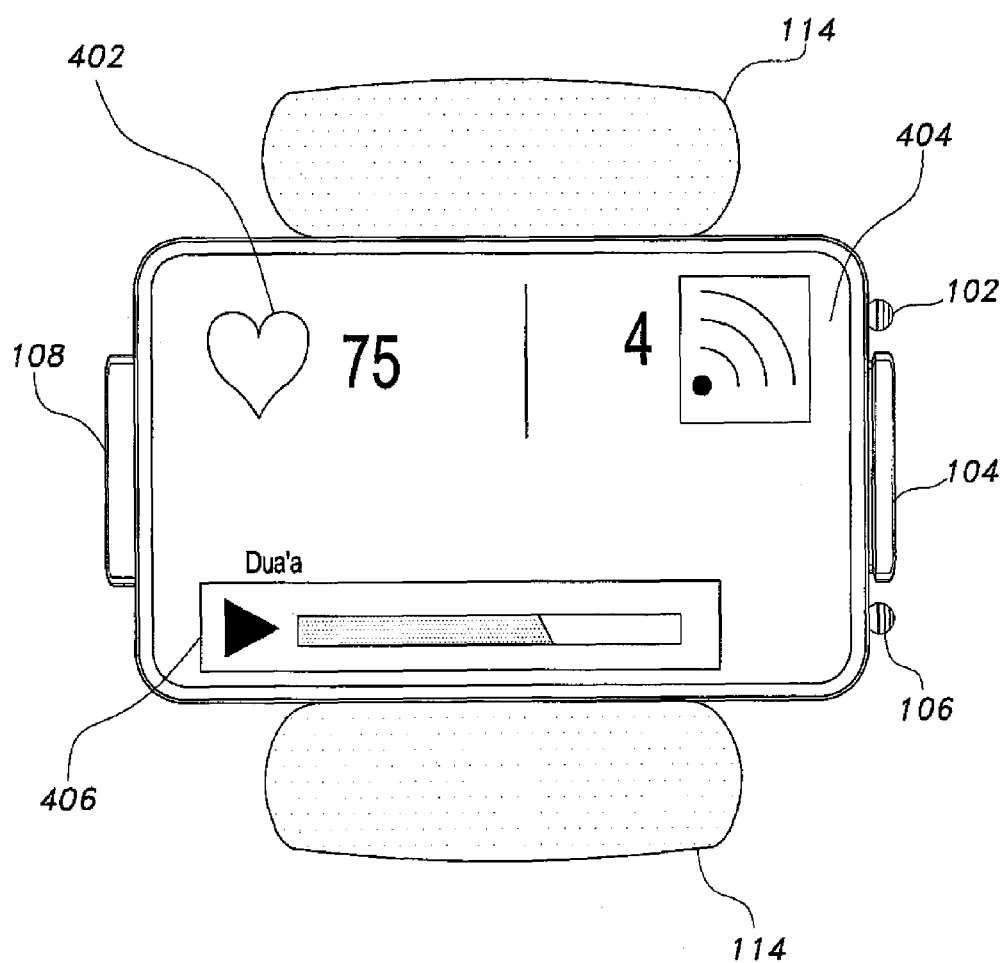
FIG. 4 is a top view of the wrist-mounted device of FIG. 1A, showing greater details thereof.

FIG. 4 shows an exemplary depiction of the wrist-mounted device 100 displaying an individual's heart rate 402, the completed rotations 404 recognized by the GPS chip, and an audio indicator 406 on the LCD display of the wrist-mounted device, such as the LCD Display 110. FIG. 4 also illustrates the watch straps 114, the LCD activation button 102, the rotation count button 104, the location button 106, and the audio control button 108. The LCD activation button 102 can switch between showing information, such as the information displayed in FIG. 4, and showing the individual age, weight and height information. The LCD activation button 102 can also switch to displaying a digital map with a designated location pinpointed by means of the GPS chip 232. Additional embodiments may include a number of preset audio or written messages on the wrist-mounted device 100, and means to allow customizable messages to be stored and recorded into the wrist-mounted device 100. The LCD display 110 can include a number of visual words, messages and symbols, such as music notes and alarm clocks, but is not limited in this regard, and additional symbols, icons, and images can be displayed.

Figure 5:
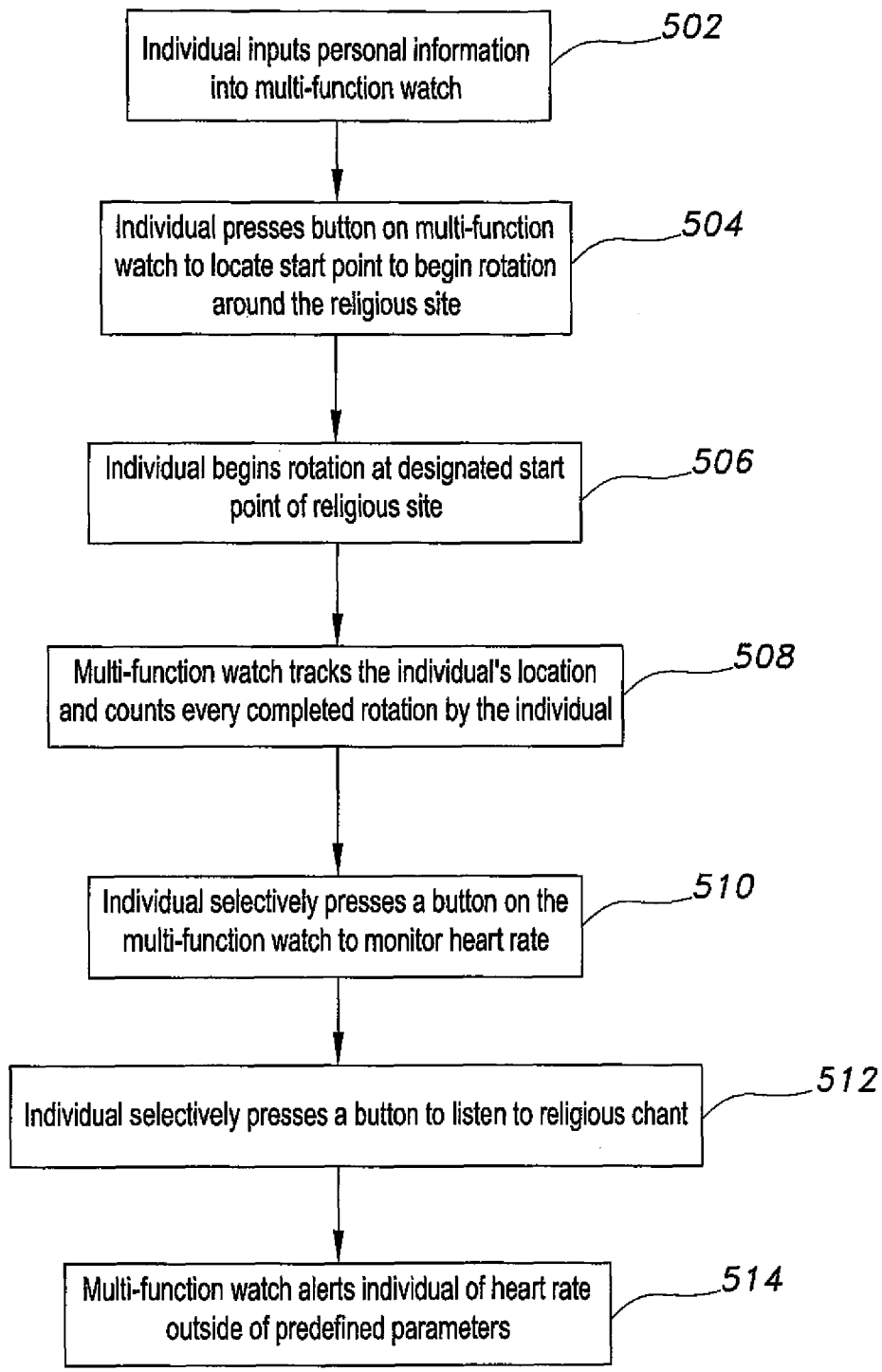
FIG. 5 is a flowchart showing selected steps in a method of using the wrist-mounted device of FIG. 1A.

FIG. 5 shows a flowchart of a logic tree 500 of an embodiment of a method for operating a wrist-mounted device to assist in performing religious rituals, such as using the general wrist-mounted device 100 of FIG. 1A and FIG. 1B. In the flowchart of the logic tree 500, at step 502 an individual inputs his or her personal information into the wrist-mounted device. The entering of information can be accomplished by means of a capacitance touch screen or multi-touch interface, as known in the art, and can incorporate the use of a digital keyboard. At step 504, the individual can press at least one button on the wrist-mounted device 100 to locate the start point to begin rotation around the religious site, such as the Kaaba.

At this step in locating the start point of the religious site, the GPS chip 232 in the wrist-mounted device is in communication with a satellite, such as the satellite 306 in FIG. 3. The GPS chip 232 can send and receive coordinates 307 to and from the satellite, such as receiving the coordinates 305 of the traditional start point of Kaaba, which is usually indicated by a green light, such as the light source 304 in FIG. 3. This green light is also indicator for the pilgrim that he or she has completed a full rotation around the holy site, such as Kaaba. The processor 222 can register each time the GPS chip 232 is in a close location to the green light as detected by sensor 112 in order to count the number of complete rotations the individual has done.

At step 506, the individual can begin the rotations around the holy site at the starting point, such as the light source 304 in FIG. 3. Continuing at step 508, the wrist-mounted device can track the individual's location and counts the completed rotations around the holy site. This is illustrated by the GPS count 404 of FIG. 4, which shows a GPS signal and a number "4" indicating the number of rotations around the start point of the holy site. In addition to the GPS chip 232 in the wrist-mounted device 100 being able to receive the coordinates 305 for the green light for detecting and counting the start point, the sensor 112 can detect the light source and color of the light source, such as a green light of the light source 304, to detect the start point for the counting the number of rotations around the holy site. This data corresponding to the detection of the light source and color of the light source by the sensor 112 can be transmitted to processor 222 to count the number of completed rotations around a holy site, such as the Kaaba. The sensors can be various sensors, including photodetectors, photosensors, cryogenic detectors, photodiode light sensors, LED photodiodes, optical detectors, photoresistors, electro-optical, wave-front sensors etc., as is known in the art. The sensors can also be wireless sensors or hardwired for communication, and is not limited in this regard.

At step 510, the individual can selectively press a button on the wrist-mounted device 100 to monitor his or her heart rate as detected by the sensor 202, such as pressing the LCD activation button 102, which will display the individual's personal information. At step 512, the individual can also selectively a press another button on the wrist-mounted device to listen to a religious chant, such as pressing the audio control button 108. The audio control button 108 can also be adapted to be adjustable to control the sound volume, with one end of the button increasing the sound volume and the opposite end decreasing the sound volume.

The flowchart concludes at step 514, as the wrist-mounted device 100 can alert individual if his or her heart rate is outside of a defined parameter. The defined parameter for the individual's heart rate is pre-programmed into the processor and is based on a variety of factors, such as the individual's age, height, weight, etc., that is entered into the wrist-mounted device 100 at step 502. If the individual's heart rate is within the parameters, the wrist-mounted device 100 will continue operating as pre-programmed.

Additional embodiments of the wrist-mounted device and the methods for operating the wrist-mounted device allow for the device to display time and date information. Additional embodiments also allow for the wrist-mounted device to maintain multiple calendars, such as the lunar and solar calendar, in order to pinpoint or highlight the holy dates of the individual's religion, such as highlighting the 8th day to the 12th day of the 12th month in the lunar calendar. The lunar calendar is 11 to 12 days shorter than the solar calendar and the holy dates of the 8th day to the 12th day of the 12th month in the lunar calendar will change every year in regard to the solar calendar.

It is to be understood that the present invention is not limited to the embodiments described above, but encompasses any and all embodiments within the scope of the following claims.

I claim:

1. A wrist-mounted device to assist individual pilgrims, comprising:
   a case;
   attachment means for attaching the case onto an individual;
   an electronic processor mounted in the case;
   an electronic display mounted in the case, the display being connected to the processor; and
   a sensor housed in the case for detecting the color of a light source, detecting the location of the light source, and transmitting data signals to the processor corresponding to the light source detected;
   wherein the light source is an indicator of a start point; and the data signals track a number of complete rotations the individual has completed around a holy site.

2. The wrist-mounted device according to claim 1, further comprising:
   a GPS chip housed in the case and connected to the processor;
   an alarm chip housed in the case and connected to the processor to provide at least one type of alert to the individual;
   an audio unit housed in the case and connected to the processor to produce at least one audio transmission; and
   a sensor housed in the attachment means to receive the individual's heart rate and to transmit data signals corresponding to the individual's heart rate to the processor.

3. The wrist-mounted device according to claim 1, wherein the display comprises an LCD display.

4. The wrist-mounted device according to claim 3, wherein the processor displays the transformed data signals onto the LCD display.

5. The wrist-mounted device according to claim 1, wherein the attachment means comprises at least one strap for attaching around the wrist of the individual.

6. The wrist-mounted device according to claim 1, further including input means on the display for inputting personal information of the individual.

7. A wrist-mounted device to assist individual pilgrims, comprising:
- a case having a strap attached thereto adapted for mounting the case onto a user's wrist;
- means mounted in the case for monitoring the user's heart rate;
- means mounted in the case for annunciating an alert when the user's heart rate exceeds a predetermined limit;
- means mounted in the case for determining the location of the case using a GPS sensor;
- means mounted in the case for displaying to the user the location of the case relative to a holy site of interest to the user;
- means mounted in the case for monitoring and displaying to the user a count of the number of user perambulations around the holy site; and
- means mounted in the case for annunciating prayers and scriptures associated with ritual observance at the holy site;
- wherein the GPS sensor provides an indication of a user location;
- wherein the means for monitoring and displaying the count of the number of complete perambulations around the holy site, and
- wherein the means for annunciating prayers and scriptures announces the prayers and scriptures for user at the tracked location of the holy site.

* * * * *